July 24, 1962 M. B. NETTLESHIP ET AL Plant Pat. 2,157
INDIGO PLANT
Filed April 10, 1961
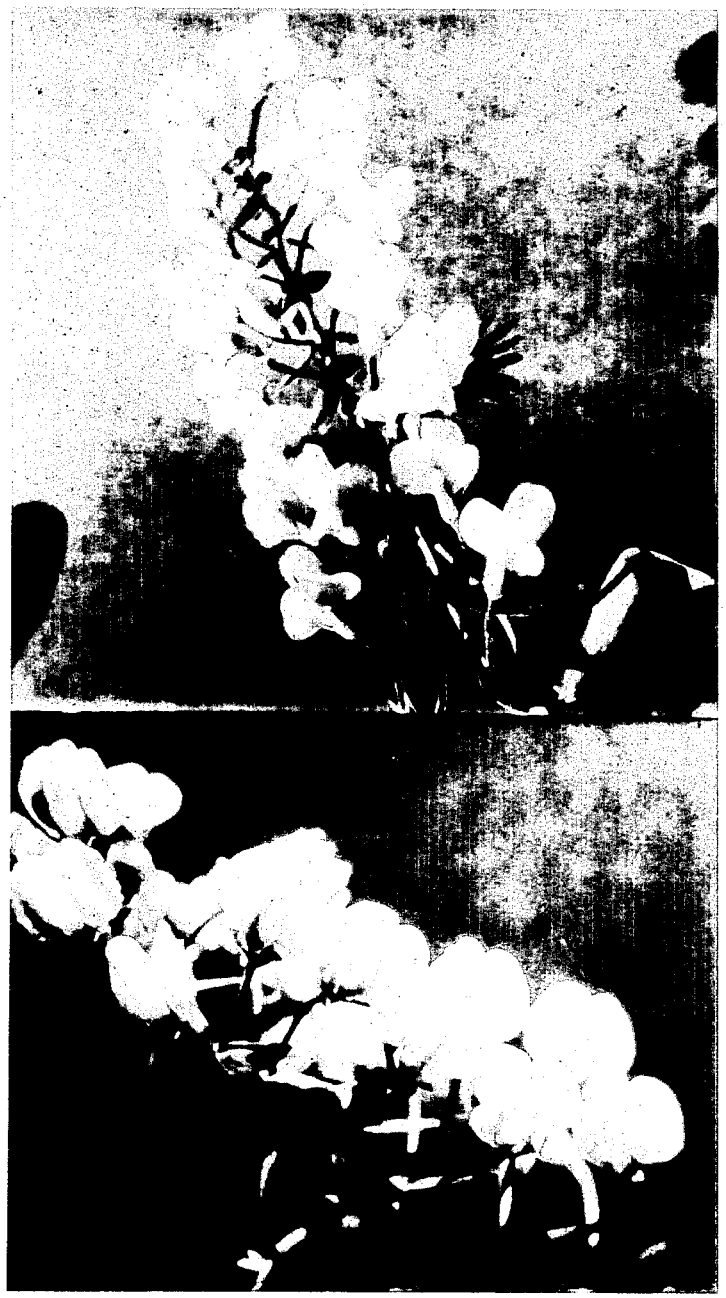
INVENTORS
ANDERSON NETTLESHIP
MAE B. NETTLESHIP
BY Adolph E. Bugin
ATTORNEY United States Patent Office Plant Pat. 2,157
Patented July 24, 1962

2,157
INDIGO PLANT

Mae B. Nettleship and Anderson Nettleship, Fayetteville, Ark., assignors to Antaeus Lineal 1948, ANL Medical Laboratory Division, Inc., a corporation of Arkansas Filed Apr. 10, 1961, Ser. No. 102,079
1 Claim. (Cl. 47—60)

This invention relates to a new and distinct variety of indigo plant of a decorative type. It was originated by careful breeding from certain wild varieties by hybridization and self-pollination, particularly from *Baptisia leucophaea,* Nutt., and *Baptisia sphaerocarpa.*

The main object of this invention was to produce a new indigo plant of early blooming qualities suitable for outdoor and garden decor and for art flower purposes.

This object was attained by selection of parents and has resulted in a strong erect plant, which grows to about 30 cm. in height, with flowers having a distinct yellow color.

In addition to the main object, the follwing characteristics are displaed by this plant:

(1) Three or more large racemes of persistant, foliaceous flowers with slender peduncles.

(2) A large quantity of blossoms gracefully placed on erect or horizontal bracts or stems.

(3) Healthy, dark green foliage which produces a well rounded low bush form and grows on all stalks.

(4) Large individual flowers with straight wings longer than their standards.

These characteristics and distinctions definitely differentiate this new variety from the wild stock from which it was derived, as well as from all other varieties of this class of plants known to the inventors. Asexual reproduction of this new variety shows that these characteristics come true to form and are established.

The accompanying illustration shows the distinctive characteristics of the flowers at different stages of development from but to full blown blossoms in colors as nearly true as is reasonably possible by the medium used.

The following detailed description of this new variety is in terminology and plate references in accordance with Color Standards and Nomenclature, Robert Ridgway, and ordinary dictionary definitions:

Classification: Decorative.

Parentage: Wild plants-unclassified, cross- and self-pollinated, seedlings of unnamed ancestry.

Cold resistance: Plant above ground until abscission at ground level in the fall or early winter, roots (rhizomes) persist and produce new plants perennially.

Blooming period: From early April throughout the summer, outdoors in the Fayetteville, Arkansas, area.

Propagation: Retains its distinguishing characteristics through succeeding propagations by layerings, cuttings, and root stocks.

*The Flower*

Locality where grown: Fayetteville, Arkansas.

Flowers borne: On racemes with sturdy four-pointed bracts.

Quantity of bloom: Three or more racemes per plant with approximately twenty individual blossoms per raceme.

Bud:

*Form.*—Spatulate, flattened perpendicularly, merging into conical to ellipsoidal shape at base; opening slowly.

*Size.*—Individual bud 1.5 to 1.8 cm.

*Bract.*—Strong, upright. From about dark green, Plate XVIII, 35′ *m;* and Apple Green, Plate XVII, 29′ GG–Y; to Pale Viridine Yellow, Plate V, 29 GG–Y, *f.*

*Color.*—Shades from about Sulphur Yellow, Plate V, 25 YG–Y, *f*; and Light Chalcedony Yellow, Plate XVII, 25 YG–Y, *d*; to about Naphthalene Yellow, Plate XVI, 23′ Yellow *f* when opening.

Bloom:

*Size.*—Individual bloom size 1.5 to 2 cm. across wing petals at base.

*Raceme.*—Individual raceme of fully opened flowers measures up to 15–18 cm. in length, 4 to 5 cm. in width. Raceme stem strong, erect but not stiff. Flowers on individual stems of 1 to 2 cm.

*Form.*—A four- or five-toothed calyx flower with spread wings, with sides reflexed and separate heel petals.

*Color.*—As flower first opens, petals shade from outer parts of petals of about Martius Yellow, Plate IV, 23 Yellow, *f*; Naphthalene Yellow, Plate XVI, 23′ Yellow, *f*; and Primrose Yellow, Plate XXX, 23″ Yellow, *d*; to base of petal of about Light Chalcedony Yellow, Plate XVII, 25′ YG–Y, *d*; and Pale Green Yellow, Plate V, 27 G–Y, *f*. When fully open shades from outer parts of petals of light Martius Yellow, Plate IV, 23 Yellow, *g*; and Naphthalene Yellow, Plate XVI, 23′ Yellow, *g*; to deeper yellow at inner parts of petals in these shades of about *f* and some Sulphur Yellow, Plate V, 25 YG–Y, *f*; and Primrose Yellow, Plate XXX, 23″ Yellow, *d*; with base of some blooms shading to about Chartreuse Yellow, Plate XXXI, 25″ YG–Y, *d*; and Light Chalcedony Yellow, Plate XVII, 25′ YG–Y, *d*.

*The Plant*

Growth: Free, strong upright on an individual stem. A number of stems come from each rooting. Grows to a normal height of about 30 cm. or more, and has been grown with stems of as much as 40 cm. in length.

Form: Grows in a pleasant globular bush shape with loose airy spacing of branches.

Stems: Strong, supple, semi-erect for each raceme, long for excellent cutting.

Foliage:

*Size.*—5 cm. or less per leaf.

*Quantity.*—The average grows on a number of divergent branches from the central stem. Grows on the plant usually to within about 15 cm. of the ground.

*Form.*—Spatulate leaves of narrow, oblong-obovate shape with conspicuous spicules.

*Color.*—Dark green, of about Plate VI, 35, Meadow Green, *k* to Plate XVIII, 35′, Killarney Green, *i*; smooth to slightly hairy leaves.

*Aspect.*—Semi-glossy.

*Comparison*

The common varieties of wild indigo, *Baptisia leucophaea,* Nutt., *B. sphaerocarpa* and others have individual blue or whitish blossoms or at most a single raceme with a few small flowers of poor quality or color characteristics. Its foliage and rootage are irregular and "scraggly." This new variety has the following outstanding differences:

(1) It has distinctively yellow flowers.

(2) It has earlier blooming, starts in early April in Fayetteville, Arkansas, area .

(3) It has more prolonged blooming season, throughout the summer months.

(4) It has year-around blooming under hothouse conditions.

(5) It has more racemes per plant.

(6) It has more blossoms per raceme.

(7) It has larger blossoms.

(8) It grows to a normal height of about 30 cm. or more.

What is claimed is:

A new and distinct variety of domestic indigo plant of a hardly decorative type substantially as herein shown and described, characterized particularly by its regular, graceful plant growth, healthy dark green foliage, which remains on the plant throughout the season; its erect, strong and large number of recemes with showy sprays of abundant blossoms on each raceme; and its excellent productivity of long-lasting highly decorative flowers of general cream-colored yellow tonality.

No references cited.